United States Patent
Campin et al.

(10) Patent No.: US 9,011,418 B2
(45) Date of Patent: *Apr. 21, 2015

(54) OPHTHALMIC DEVICE POSITIONING SYSTEM AND ASSOCIATED METHODS

(75) Inventors: John A. Campin, Orlando, FL (US); John J. Bowes, Orlando, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 2531 days.

This patent is subject to a terminal disclaimer.

(21) Appl. No.: 11/493,081

(22) Filed: Jul. 26, 2006

(65) Prior Publication Data
US 2007/0027442 A1   Feb. 1, 2007

Related U.S. Application Data

(60) Provisional application No. 60/703,618, filed on Jul. 29, 2005.

(51) Int. Cl.
*A61F 9/008* (2006.01)
*A61B 3/15* (2006.01)
*A61B 3/10* (2006.01)

(52) U.S. Cl.
CPC .............. *A61B 3/152* (2013.01); *A61B 3/1015* (2013.01)

(58) Field of Classification Search
None
See application file for complete search history.

(56) References Cited

U.S. PATENT DOCUMENTS

| | | | |
|---|---|---|---|
| 5,796,859 A * | 8/1998 | Mammone | 382/128 |
| 6,280,436 B1 * | 8/2001 | Freeman et al. | 606/5 |
| 6,532,298 B1 * | 3/2003 | Cambier et al. | 382/117 |
| 2002/0005862 A1 * | 1/2002 | Deering | 345/694 |
| 2005/0105044 A1 | 5/2005 | Warden | |

FOREIGN PATENT DOCUMENTS

| | | |
|---|---|---|
| GB | 2 359 375 A | 8/2001 |
| JP | 5-207352 | 8/1993 |
| JP | 9-103408 | 4/1997 |
| JP | 9-149914 | 6/1997 |
| JP | 2001-275033 | 10/2001 |
| JP | 2002-94865 | 3/2002 |

(Continued)

OTHER PUBLICATIONS

UK Patent Publication, Aug. 2001, GB, Marshall.*

(Continued)

*Primary Examiner* — Lynsey Crandall
(74) *Attorney, Agent, or Firm* — Darien Reddick (57) ABSTRACT

A system and method for determining an optimal position of an eye relative to an ophthalmic device are disclosed. One embodiment of the method includes receiving data comprising an image of a surface of an eye with the eye at a first position relative to an ophthalmic device. An edge feature in the image is located, and a sharpness calculation on the edge feature is performed using a predetermined algorithm to yield a sharpness value. The eye surface is then adjusted to a second position relative to the ophthalmic device, and the previous steps are repeated until the sharpness value is maximized, which is an indication that an optimal eye position has been achieved. An embodiment of the system includes a processor and a software package executable by the processor, the software package adapted to perform the calculations as above. Means are also provided for adjusting the eye surface to a second position relative to the ophthalmic device.

23 Claims, 5 Drawing Sheets

(56) References Cited

FOREIGN PATENT DOCUMENTS

| | | | | |
|---|---|---|---|---|
| JP | 2002-334325 | 11/2002 | | |
| JP | 2005-095354 | 4/2005 | | |
| JP | 2005/177166 | 7/2005 | | |
| JP | 2006-333902 | 12/2006 | | |
| WO | WO 01/60241 A1 | 8/2001 | | |
| WO | WO 03/053228 A2 | 7/2003 | | |
| WO | WO 2005048829 A2 * | 6/2005 | ............. | A61B 3/103 |
| WO | 2007/016231 | 2/2007 | | |

OTHER PUBLICATIONS

International Search Report for PCT/US2006/029169, Publication No. WO2007016231, dated Dec. 18, 2006, 3 pages.

International Preliminary Report on Patentability for PCT/US2006/029169, Publication No. WO2007016231, dated Jun. 22, 2007, 6 pages.

* cited by examiner

OPHTHALMIC DEVICE POSITIONING SYSTEM AND ASSOCIATED METHODS

This application claims priority from provisional U.S. Patent Application Ser. No. 60/703,618, filed Jul. 29, 2005.

TECHNICAL FIELD OF THE INVENTION

The present invention relates to systems and methods for performing corneal wavefront measurements and laser-assisted corneal surgery, and, more particularly, to such systems and methods for optimizing a focus of the eye undergoing such surgery.

BACKGROUND OF THE INVENTION

It is known in the art to perform corneal ablation by means of wavefront-guided refractive laser surgery. Typically a wavefront sensor measures an aberration map and its position relative to anatomical landmarks, which can be intrinsic or externally applied features. Aberration data, sometimes along with geometric registration information, can be transferred directly to a treatment excimer laser, which is typically used to perform the ablation.

In ophthalmic devices, the positioning of a measuring or ablation device a known distance from, and correctly aligned to, an eye, such that the device can be therapeutically effective, is of great importance. In some systems the eye must be centered and in clear focus for interaction of the image with an operator. It can also be important for a laser beam to come to focus at a predetermined plane with respect to the eye, for example, in an excimer laser system, or to have the eye positioned for an effective subsequent measurement of the eye, for example, a wavefront measurement.

Among the known techniques for assisting in positioning an ophthalmic device are the breaking of a plurality of light beams, such as infrared light beams, by the corneal apex, and the projection onto the cornea of a plurality of light beams, which can subsequently be analyzed either automatically or by an operator to assess accuracy of eye positioning. If the eye is deemed not to be in a therapeutically effective position, then the device and/or head/eye can be moved so as to reposition the eye optimally or to within defined acceptable tolerances.

Known current approaches to solving the positioning problem are typically subject to error and require intervention by an operator and/or additional hardware. Therefore, it would be advantageous to provide a system and method for improving accuracy and automation in eye alignment, without the need for human operator input or for additional hardware.

BRIEF SUMMARY OF THE INVENTION

The present invention is directed to a system and method for determining an optimal position of an eye relative to an ophthalmic device. An optimal position can be any position that places the eye such that the ophthalmic device can be therapeutically effective in its designed for purpose. Optimal positioning can include positioning the eye such that the ophthalmic device can perform to the limits of its design tolerances, as well as anywhere in the ophthalmic devices designed for therapeutically effective range. For example, an optimal position can be a position in which an image of a selected feature of the eye is at a best focus achievable with the ophthalmic device within any incremental positioning constraints. An embodiment of the method of the present invention comprises the step of receiving data comprising an image of a surface of an eye with the eye at a first position relative to an ophthalmic device. An edge feature in the image is located, and a sharpness calculation on the edge feature is performed using a predetermined algorithm to yield a sharpness value. The eye surface is then adjusted to a second position relative to the ophthalmic device, and the previous steps are repeated until the sharpness value is maximized based on the predetermined algorithm, which is one indication that an optimal eye position has been achieved. In the case of a focusing parameter, for example, a positioning adjustment can be made incrementally in a first direction until a sharpness value, goes through a maximum value and then begins to decrease, indicating that the optimal focus position has been passed through. A positioning adjustment in a second direction opposite to the first can then be made to return to the position at which the sharpness value was determined to have achieved the maximum value.

An embodiment of the system for determining an optimal position of an eye relative to an ophthalmic device in accordance with the present invention can comprise a processor and a software package executable by the processor. The software package is adapted to perform the calculations as above. Means are also provided for adjusting the eye surface to a second position relative to the ophthalmic device. The software package then receives the new image data on the eye in the second position, and the calculational steps are repeated until the sharpness value is maximized in accordance with a predetermined algorithm. Maximizing the sharpness value is one indication that an optimal eye position has been achieved.

Embodiments of the system and method of the present invention have an advantage that no additional hardware is required if the ophthalmic device already comprises means for imaging the surface of the eye and for capturing that image. An additional element can comprise a software package for computing optimal centering and focal position, and for either indicating a required ophthalmic device movement, or for driving the ophthalmic device position depending upon the presence of an automatic positioning capability.

In cases in which it is desired for either the software or an operator to interact with the image, it is preferable that features in the image be as sharp as possible, within the limits of the ophthalmic device. Embodiments of the present invention can optimize focus by maximizing the clarity of the features in the image.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

A description of the preferred embodiments of the present invention will now be presented with reference to FIGS. 1-6C. An exemplary embodiment eye positioning system 10 is depicted schematically in FIG. 1, and an exemplary method 100, in FIGS. 2A and 2B.

Figure 1:
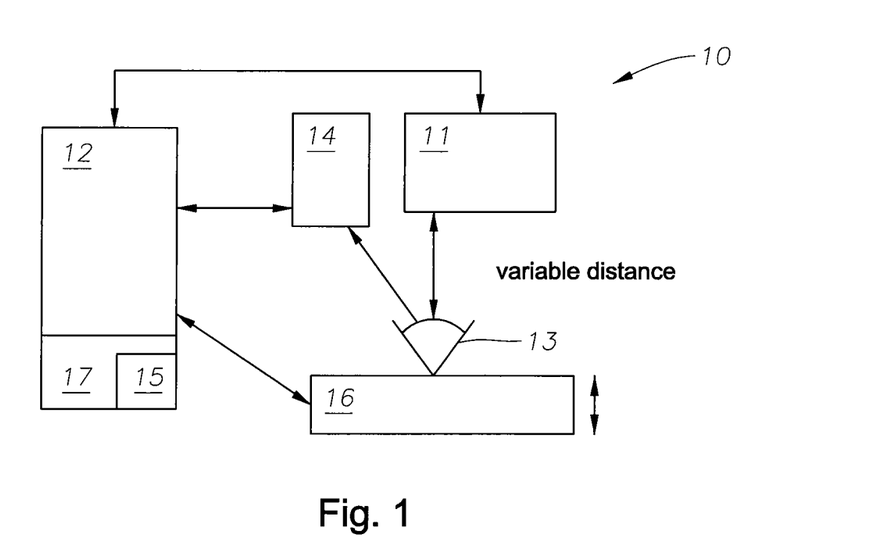
FIG. 1 is a schematic of one embodiment of the eye positioning system of the present invention.
Figure 2A:
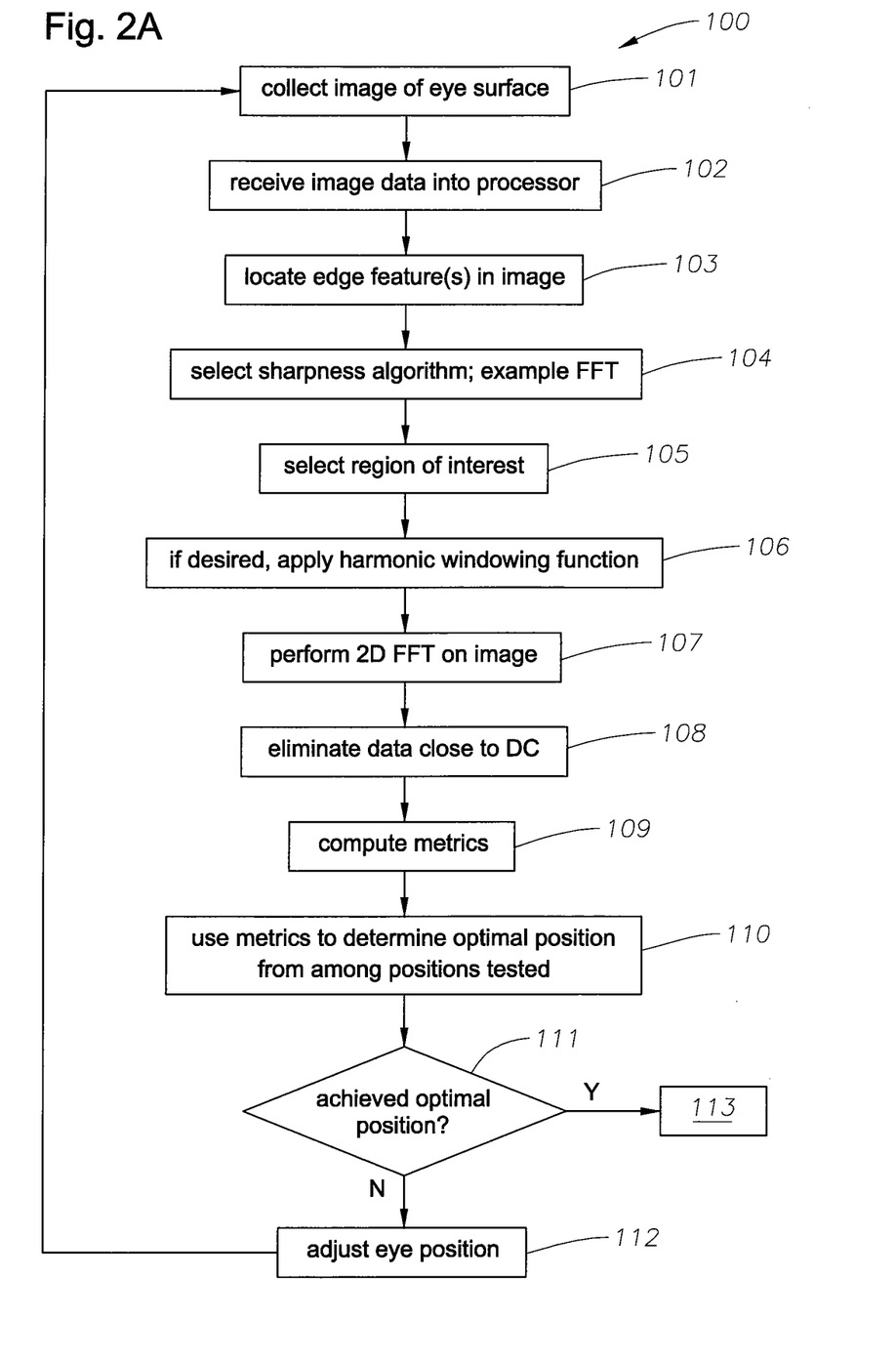
FIGS. 2A and 2B provide a flowchart of an exemplary embodiment of the method of the present invention, for the case of a fast Fourier transform sharpness algorithm.

An embodiment 100 of the method for determining an optimal (therapeutically effective) position of an eye relative to an ophthalmic device 11 comprises the step of receiving data into a processor 12 (block 102). The data comprise an image of a surface of an eye 13 that has been collected with, for example, a video camera, digital camera, still camera or frame grabber 14, in communication with the processor 12. The image is collected with the eye at a first position relative to the ophthalmic device 11 (block 101). Ophthalmic device 11 can be, for example, and without limitation, a femtosecond laser microkeratome, a treatment laser, such as an excimer laser, an aberrometer, or any other ophthalmic device as will be known to those familiar with the art for which accurate positioning of an eye may be required.

A software package 15, which can be resident in a memory 17 (here shown as part of processor 12), includes a code segment for locating an edge feature in the image (block 103). Memory 17 can be a separate memory operably coupled to processor 12, or can be an integral part of processor 12. The edge feature may include, but is not intended to be limited to, a scleral blood vessel or a feature of the iris. It is assumed that a well-focused image of the eye has relatively sharp edges, and thus that the selected eye feature is most clearly defined when the image is in focus. When the image is somewhat out of focus, the image is softened, and the edges of these features are less clear. Further, when the image has clearly defined edges, then the amount of high-frequency information in the image is higher.

Processor 12 (control circuit) may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory 17 coupled to the processor 12 or control circuit may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the microprocessor or control circuit implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the microprocessor or control circuit executes, operational instructions (e.g., software package 15) corresponding to at least some of the steps and/or functions illustrated and described in association with FIGS. 2A and 2B.

Software package 15 can also comprise a code segment operable to cause processor 12 to perform a sharpness calculation on the edge feature using a predetermined sharpness function algorithm to yield a sharpness value. The sharpness function algorithm is selected at block 104. The algorithm may include, but is not intended to be limited to, an estimate of image grey-level variance and amplitude, a computation of an intensity difference between adjacent regions of the image, a histogram-based approach, an edge-detection mask such as a Laplacian, and a Fourier transform function. The sharpness function algorithm may be selected, for example, based upon image attributes, frequency with which the algorithm is to be applied, and/or accuracy requirements.

As an example of the criteria used for selecting an algorithm, Fourier transform-based approaches yield a large amount of detailed data, and very sophisticated functions can be developed and fine-tuned to optimally address a defined problem. However, Fourier transforms of large images require a significant number of computations, and the relatively large amount of time taken to perform the processing can be problematic in certain applications.

Conversely, pixel intensity difference functions such as:

$$\sum |I(x, y) - I(x, y-1)| + \sum |I(x, y) - I(x+1, y)|$$

have relatively minimal computational issues, but lack the flexibility of the Fourier-based approach. Therefore, different functions may be preferred depending upon the specific implementation details and requirements. Such different functions will be known to those having skill in the art and are contemplated to be within the scope of the present invention.

Although not intended as a limitation, a Fourier-based approach will now be discussed. By computing a Fourier transform, typically a fast Fourier transform, of the area or areas of interest on the image, the amount of information present in the higher spatial frequencies can be determined. By setting the device-to-eye distance such that the high spatial frequency content is maximized, the image focus can be optimized, and thus the eye-to-device distance is also optimized (e.g., the ophthalmic device will be therapeutically effective to the limits of the device).

Figure 3:
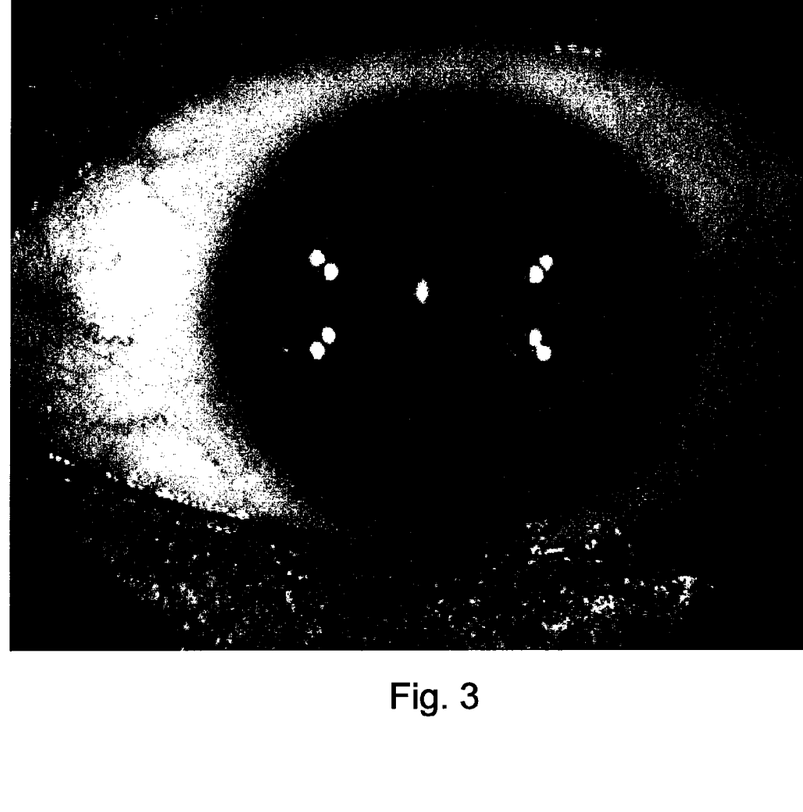
FIG. 3 is an in-focus image of an eye.
Figure 4A:
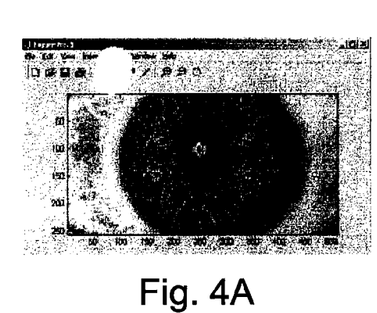
FIGS. 4A-4J are eye images ranging from sharpest to most blurred (FIGS. 4A-4E), along with the corresponding fast Fourier transform plots (FIGS. 4F-4J)
Figure 4B:
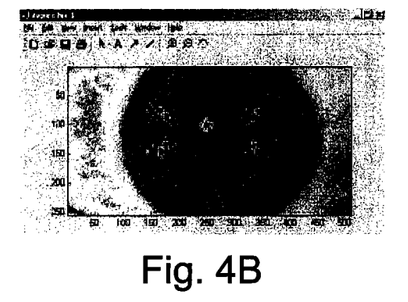
Figure 4C:
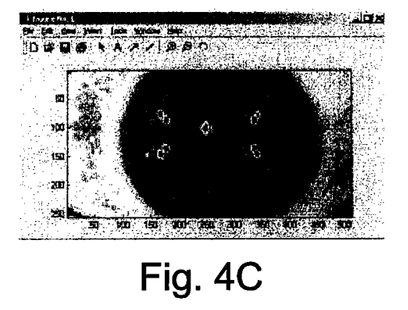
Figure 4D:
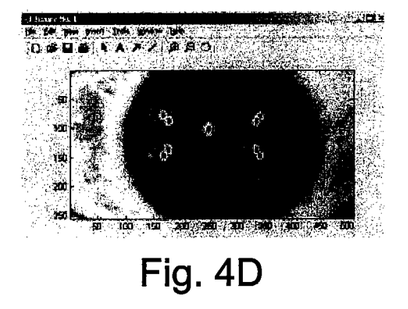
Figure 4E:
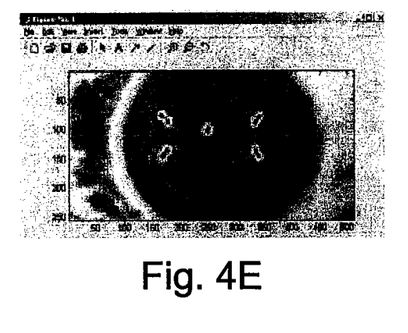
Figure 4F:
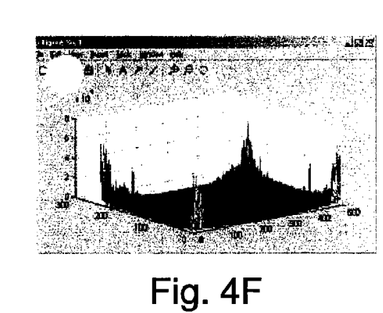
Figure 4G:
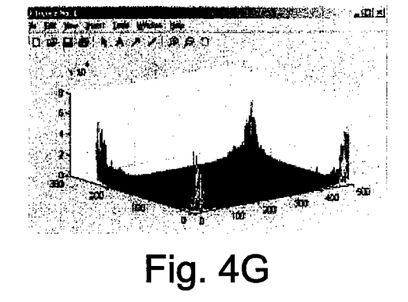
Figure 4H:
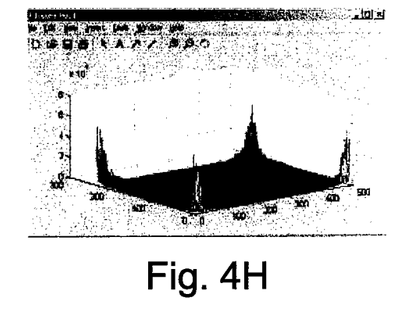
Figure 4I:
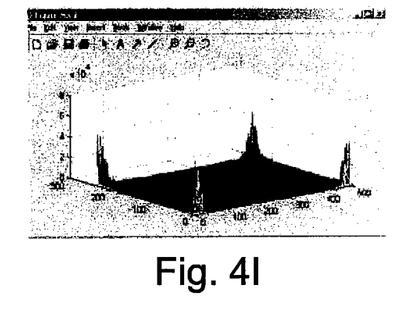
Figure 4J:
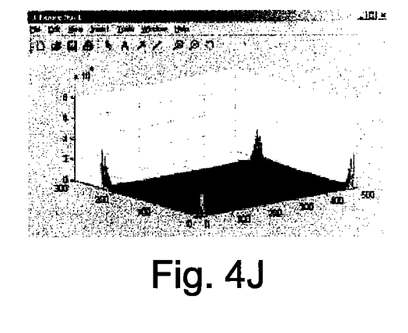

FIG. 3 illustrates a typical image of an eye captured on a wavefront sensor. This eye is well focused, and scleral and iris features are clearly visible. A region of interest is selected from the image, and from images of the same eye in various degrees of de-focus (block 105). Preferably an area is selected that does not contain eyelids or eyelashes. Multiple regions can be used if desired, such as different regions on the sclera (for example, to the left, right, above, and below the sclera), regions from the iris, or combinations of these. The software package 15 may also comprise an algorithm for selecting area(s) of interest which can automatically eliminate artifacts in the image, such as images of the light source.

A two-dimensional fast Fourier transform (FFT) is performed on each of the images (block 107). The dominant feature in the FFTs is the dead-center ("DC") value and those values close to DC. These are of no interest in the present case, but may be used to normalize data. FIGS. 4A-4E are pseudo-color plots of each of the images, from sharpest (FIG.

4A) to most blurred (FIG. 4E) and the corresponding FFTs are provided in FIGS. 4F-4J. In this exemplary calculation, the FFT sizes used are 256×512, although this is not intended as a limitation. In these plots, the data close to DC are eliminated in order to make the medium- and high-frequency content easier to see (block 108). In these plots, the highest-frequency components are in the center, and so the data of interest are away from the corners. It can be seen that, as the image becomes more blurred, the plots are flatter away from the corners; that is, there is less information at the medium and higher frequencies.

In an alternate embodiment, a harmonic windowing function, such as a Hamming window, can be applied to the region(s) of interest prior to the FFT (block 106). In addition to a beneficial reduction of harmonic artifacts that is achieved from such an operation, a sensitivity of the invention to slight decentration or shift of the region(s) that could result from uncompensated eye movement can be reduced. This benefit is achieved since data near the periphery of the region(s) are maximally attenuated by the windowing function.

Figure 2B:
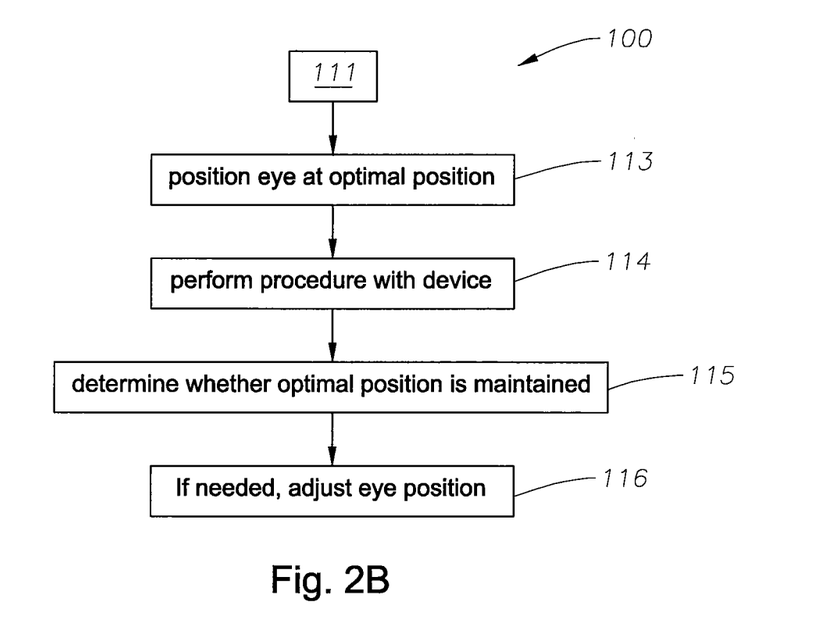
Figure 5:
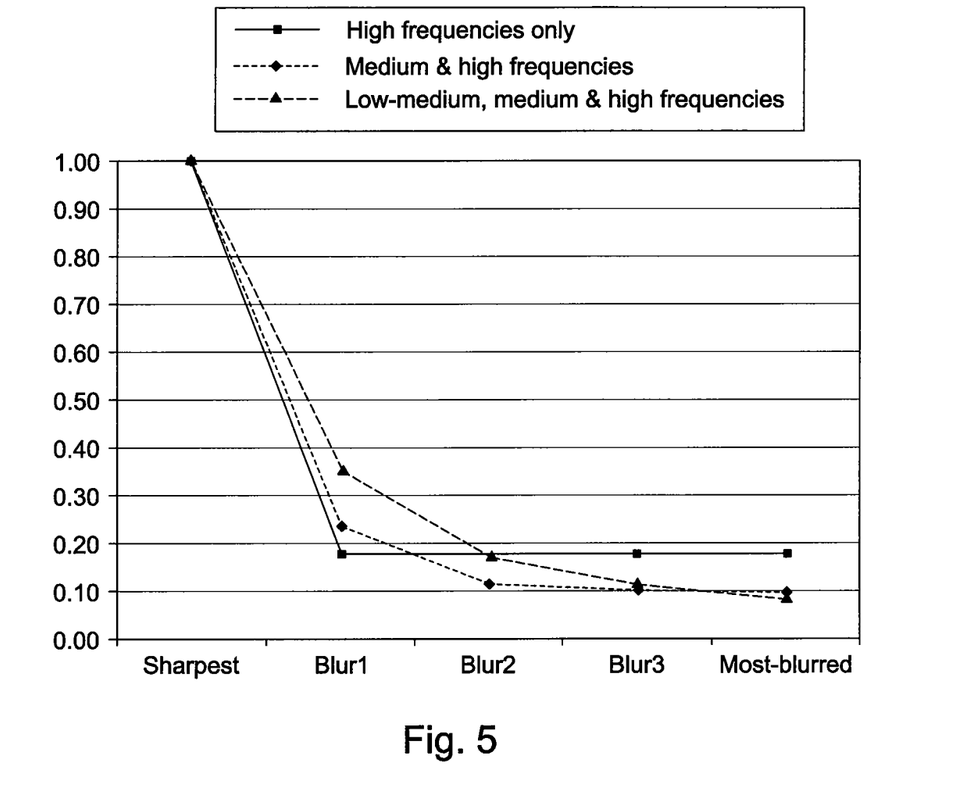
FIG. 5 is a plot of the variation in the medium- and higher-frequency spectral content versus the level of image blur.

In an exemplary embodiment, metrics can be computed (block 109) comprising the integral over the FFT from a lower frequency out to the maximum frequency in the data. The lower-frequency values are varied so as to increase or decrease the amount of data used in computing the integral. These metrics are normalized so as to have a peak value of 1.0, as shown in the plot of FIG. 5. It can be seen that, when only the highest-frequency components are used (■), the metric is extremely sensitive to even minor amounts of blurring. These data are beneficial for precisely determining when the object is in best focus. However, this metric cannot be used to discriminate between images with different but modest levels of blur, because the value becomes effectively constant (the line in FIG. 5 is flat) after even a small amount of blur. The integrals that include somewhat lower frequencies show differences for each image at higher levels of blur, and so can be used to discriminate between more blurred images, but are somewhat less for the minimal blur case. Optimal metrics, therefore, account for this type of variation and can combine information from different frequencies such that they can be used to discriminate between both large and small levels of blur (block 110). It will be understood by one of skill in the art that this example of straight integration is just one of many possible approaches.

Figure 6A:
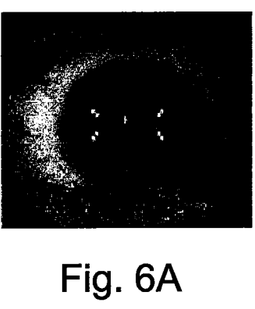
FIGS. 6A-6C are eye images, including lashes and lids, showing the difference between minimal blurring (FIG. 6A) and the maximal blurring (FIG. 6C) used in FIG. 5.
Figure 6B:
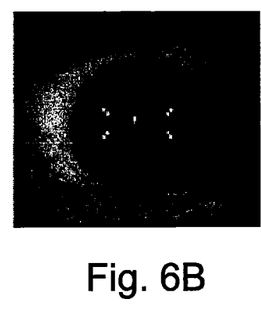
Figure 6C:
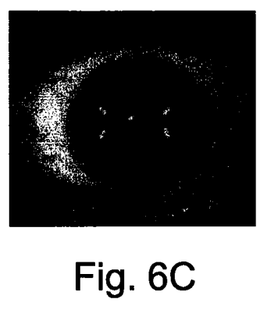

FIGS. 6A-6C illustrate some full images in grey scale to illustrate how little difference there appears to be between the initial (FIG. 6A) and minimally blurred (FIG. 6B) images. This shows the extreme sensitivity of the invention when looking at just higher-frequency information. Also shown in FIG. 6C is the maximally blurred case from the examples.

The example presented herein indicates how the post-FFT data have the information necessary to facilitate optimal device-to-eye positioning.

In use, eye surface images can be taken a plurality of times (e.g., if the desired position is not achieved) (block 111), with the eye surface 13 being adjusted to a second position relative to the ophthalmic device 11 (block 112), and the previous steps are repeated until the sharpness value is maximized, which is an indication that an optimal eye position has been achieved.

Once this position is determined, the eye 13 is positioned at the determined position (block 113). Positioning the eye can be effected manually or automatically under control of the software 15 and processor 12, by means which will be familiar to those skilled in the art and which are intended to be within the scope of the present invention, such as by using a positioning device 16. For example, and without limitation, the patient can be manually positioned, the ophthalmic device can be manually positioned, and/or the ophthalmic device or table/chair (e.g., positioning device 16) on which the patient is being supported can be automatically positioned by mechanical and electrical control systems, or any combination of these methods. Once the eye is in the desired position, a desired procedure can be performed on the eye 13 using the ophthalmic device 11 (block 114).

During the procedure, it may also be desirable to determine that an optimal eye position is maintained (block 115) using the procedure outlined above, in which case an additional adjustment to the eye position may be made if needed (block 116).

It is contemplated that positioning errors may be displayed to an operator, for example, in units of length. The information may also be used to inhibit or pause a procedure until a calibration step is performed. In addition, the information may be used to vary the device-to-eye distance a small, known amount around the optimal position prior to commencing the procedure, in order to relate spectral (post-FFT) data to distance errors.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for determining an optimal position of an eye relative to an ophthalmic device comprising the steps of:
   (a) receiving data comprising an image of a surface of an eye with the eye at a first position relative to an ophthalmic device;
   (b) locating an edge feature in the image, the edge feature being selected from a group consisting of a scleral blood vessel and an iris feature;
   (c) performing a sharpness calculation on the edge feature using a predetermined algorithm to yield a sharpness value; and
   (d) adjusting the eye surface to a second position relative to the ophthalmic device based on the sharpness calculation on the edge feature; and
   (e) repeating steps (a)-(d) until the sharpness value is maximized, wherein in each subsequent cycle the first position of step (a) is the second position of step (d) from the previous cycle and the second position of step (d) is a new position, indicating that an optimal eye position has been achieved.

2. The method recited in claim 1, wherein the predetermined algorithm is selected from a group consisting of an estimate of image grey-level variance and amplitude, a computation of an intensity difference between adjacent regions of the image, a histogram-based approach, an edge-detection mask, and a Fourier transform function.

3. The method recited in claim 1, wherein the predetermined algorithm comprises a fast Fourier transform.

4. The method recited in claim 3, wherein the sharpness calculation comprises the steps of screening the image data to preferentially retain medium- and high-frequency image data and determining an amount of retained medium- and high-frequency content, and wherein a determination of an optimal eye position comprises selecting an eye position wherein the determined amount of retained medium- and high-frequency image data is maximum.

5. The method recited in claim 3, further comprising the step, prior to the use of the fast Fourier transform, of applying a harmonic windowing function to a region of the image containing the edge feature.

6. The method recited in claim 3, wherein the sharpness value maximizing step comprises using information obtained from the fast Fourier transform at a plurality of frequency values to enable a discrimination of different levels of focus in the image.

7. The method recited in claim 1, further comprising the step of, in the event the eye is not already at the determined optimal eye position, following the maximization of the sharpness value, positioning the eye at the optimal eye position.

8. The method recited in claim 7, wherein the positioning step is performed by one of a manual adjustment and an automatic adjustment of the eye position.

9. The method recited in claim 7, further comprising the step of performing a desired procedure on the eye with the ophthalmic device.

10. The method recited in claim 7, further comprising, during the desired procedure performing step, of repeating steps (a)-(e) and the eye positioning step to ensure that an optimal eye position is maintained.

11. A system for determining an optimal position of an eye relative to an ophthalmic device comprising:
a processor adapted to:
    (a) receive data via the processor comprising an image of a surface of an eye with the eye at a first position relative to an ophthalmic device;
    (b) locate an edge feature in the image, the edge feature being selected from a group consisting of a scleral blood vessel and an iris feature; and
    (c) perform a sharpness calculation on the edge feature using a predetermined algorithm to yield a sharpness value; and
means for adjusting the eye surface to a second position relative to the ophthalmic device based on the sharpness calculation on the edge feature;
wherein the processor is further adapted to:
    (d) repeat (a)-(c) after an eye surface adjustment to the second position until the sharpness value is maximized, wherein in each subsequent cycle the first position of (a) is the second position of (d) from the previous cycle and the second position of (d) is a new position, indicating that an optimal eye position has been achieved.

12. The system recited in claim 11, wherein the predetermined algorithm is selected from a group consisting of an estimate of image grey level variance and amplitude, a computation of an intensity difference between adjacent regions of the image, a histogram-based approach, an edge-detection mask, and a Fourier transform function.

13. The system recited in claim 11, wherein the predetermined algorithm comprises a fast Fourier transform.

14. The system recited in claim 13, wherein the sharpness calculation is performed by screening the image data to preferentially retain medium- and high-frequency image data and determining an amount of retained medium- and high-frequency content, and wherein a determination of an optimal eye position comprises selecting an eye position wherein the determined amount of retained medium- and high-frequency image data is maximum.

15. The system recited in claim 13, wherein the software package is further adapted to, prior to the use of the fast Fourier transform, apply a harmonic windowing function to a region of the image containing the edge feature.

16. The system recited in claim 13, wherein the sharpness value maximization is achieved by using information obtained from the fast Fourier transform at a plurality of frequency values to enable a discrimination of different levels of focus in the image.

17. The system recited in claim 11, further comprising means for, in the event the eye is not already at the determined optimal eye position, following the maximization of the sharpness value, positioning the eye at the optimal eye position.

18. The system recited in claim 17, wherein the eye-positioning means comprises one of means for effecting a manual adjustment and means in communication with the processor for effecting an automatic adjustment of the eye position.

19. The system recited in claim 17, wherein the software package is further adapted to direct the ophthalmic device to perform a desired procedure on the eye.

20. The system recited in claim 17, wherein the software package is further adapted to, during the performance of the desired procedure, repeat (a)-(d) to ensure that an optimal eye position is maintained.

21. A method for determining an optimal position of an eye relative to an ophthalmic device comprising the steps of:
    (a) receiving data comprising an image of a surface of an eye with the eye at a first position relative to an ophthalmic device;
    (b) locating an edge feature in the image, the edge feature being selected from a group consisting of a scleral blood vessel and an iris feature;
    (c) performing a sharpness calculation on the edge feature using a predetermined algorithm to yield a sharpness value; and
    (d) adjusting the eye surface to a second position relative to the ophthalmic device based on the sharpness calculation on the edge feature; and
    (e) repeating steps (a)-(d) until the sharpness value is maximized, indicating that an optimal eye position has been achieved.

22. The method of claim 21, wherein receiving data comprising an image of a surface of an eye with the eye at a first position relative to an ophthalmic device comprises receiving the image of the surface of the eye with an optical device selected from a group consisting of a video camera, a digital camera, a still camera, and a frame grabber.

23. The method of claim 21, wherein receiving data comprising an image of a surface of an eye with the eye at a first position relative to an ophthalmic device comprises receiving the image of a surface of the surface of the eye that excludes eyelids or eyelashes.

* * * * *